United States Patent [19]

Svensson

[11] 4,431,424
[45] Feb. 14, 1984

[54] ARRANGEMENT IN A STERILIZING COUPLING

[76] Inventor: Jan A. Svensson, Solhemsgatan 12, S-561 35 Huskvarna, Sweden

[21] Appl. No.: 369,014
[22] PCT Filed: Aug. 12, 1980
[86] PCT No.: PCT/SE80/00202
  § 371 Date: Apr. 9, 1982
  § 102(e) Date: Apr. 9, 1982
[87] PCT Pub. No.: WO82/00698
  PCT Pub. Date: Mar. 4, 1982
[51] Int. Cl.³ .............................................. A61M 5/00
[52] U.S. Cl. ........................................ 604/33; 604/200; 604/905; 251/149.9
[58] Field of Search ................... 604/33, 87, 148, 200, 604/201, 244, 306, 905, 122; 251/149.9

[56] References Cited

U.S. PATENT DOCUMENTS 3,201,148  8/1965  Shurtleff .
4,022,205  5/1977  Tenczar .............................. 604/905

FOREIGN PATENT DOCUMENTS

WO80/01310  6/1980  PCT Int'l Appl. .
WO80/01507  7/1980  PCT Int'l Appl. .
314259  9/1969  Sweden .
1453634  10/1976  United Kingdom .
2008705  6/1979  United Kingdom .

Primary Examiner—Stephen C. Pellegrino
Attorney, Agent, or Firm—Cushman, Darby & Cushman

[57] ABSTRACT

Arrangement permitting sterilization during engagement of two coupling components.

One coupling component comprises a coupling element (1) and the other a coupling housing (2) capable of connection thereto. The arrangement in accordance with the invention comprises a flexible casing arrangement (6) which surrounds at least one part of the coupling element (1). A disinfectant (9) is contained inside the casing arrangement. The casing arrangement is provided with a seal (6a, 7) to interact with an abutment (8) on the coupling housing (2) during an introductory coupling movement between the components, the casing arrangement (6) being capable of being rolled or pulled along the outside of the coupling element (1) during the progressive engagement between the coupling components until they reach a fully engaged position (FIG. 1).

3 Claims, 4 Drawing Figures

ARRANGEMENT IN A STERILIZING COUPLING

The present invention relates to an arrangement in a sterilizing coupling, more precisely to a coupling of the type described and illustrated in the International Application PCT/SE80/00019.

Thus, in conjunction with FIG. 11 of the drawings in said International application, a coupling is shown in which a sterilizing action is obtained by utilizing a sealing ring prepared with a disinfectant, which gives off disinfectant to the coupling component which comes into contact with the ring during engagement. When using couplings of this type e.g. in conjunction with dialysis procedures the demands for sterility are extremely great.

The object of the present invention is thus to provide a coupling of the type referred to in the International Application PCT/SE80/00019, which is self-sterilizing during use. This object is achieved in accordance with the present invention in that the coupling has obtained the characteristics specified in claim 1.

To illustrate the invention this will be described in more detail in the following with reference to the accompanying drawings, in which FIG. 1 shows a vertical section of the coupling in accordance with the invention before the coupling element is connected to the coupling housing;

Figure 1:
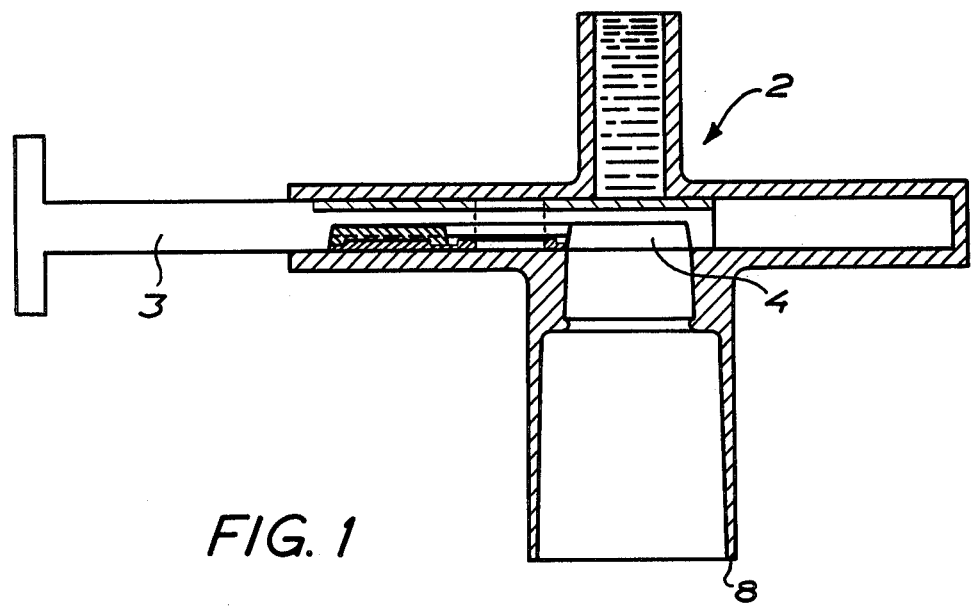
Figure 1:
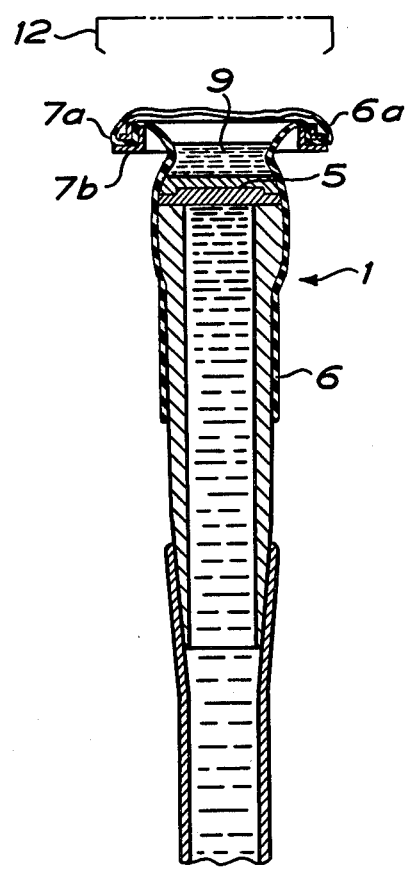

FIG. 1 shows the coupling element 1 and coupling housing 2 in a disengaged position. The coupling housing has a movable slide 3 in which at least one recess 4 is arranged for accommodating a cover, and the coupling element 1 has a cover 5 which is received for displacement in a groove. The more detailed design of the coupling is disclosed in the International Application PCT/SE80/00019.

The new feature of the coupling in accordance with the present invention is the arrangement of a casing 6 which is located around the coupling element 1. The casing 6 is preferably made from an elastic material, e.g. latex rubber, and extends up and over the cover 5. Two ring-shaped elements 7a and 7b with L-shaped cross section are arranged on both sides of the casing adjacent to the free end 6a of the casing 6. Instead of the two ring-shaped elements 7a and 7b a reinforcement can be moulded into the casing 6, which—similar to the elements 7a and 7b—is pushed in and sealingly rests against the internal peripheral surface of an abutment 8.

Inside the upper section of the casing 6 there is a disinfectant, e.g. spirit, which forms a barrier in respect of bacteria and also has a sterilizing effect on the coupling components during their engagement.

Figure 2:
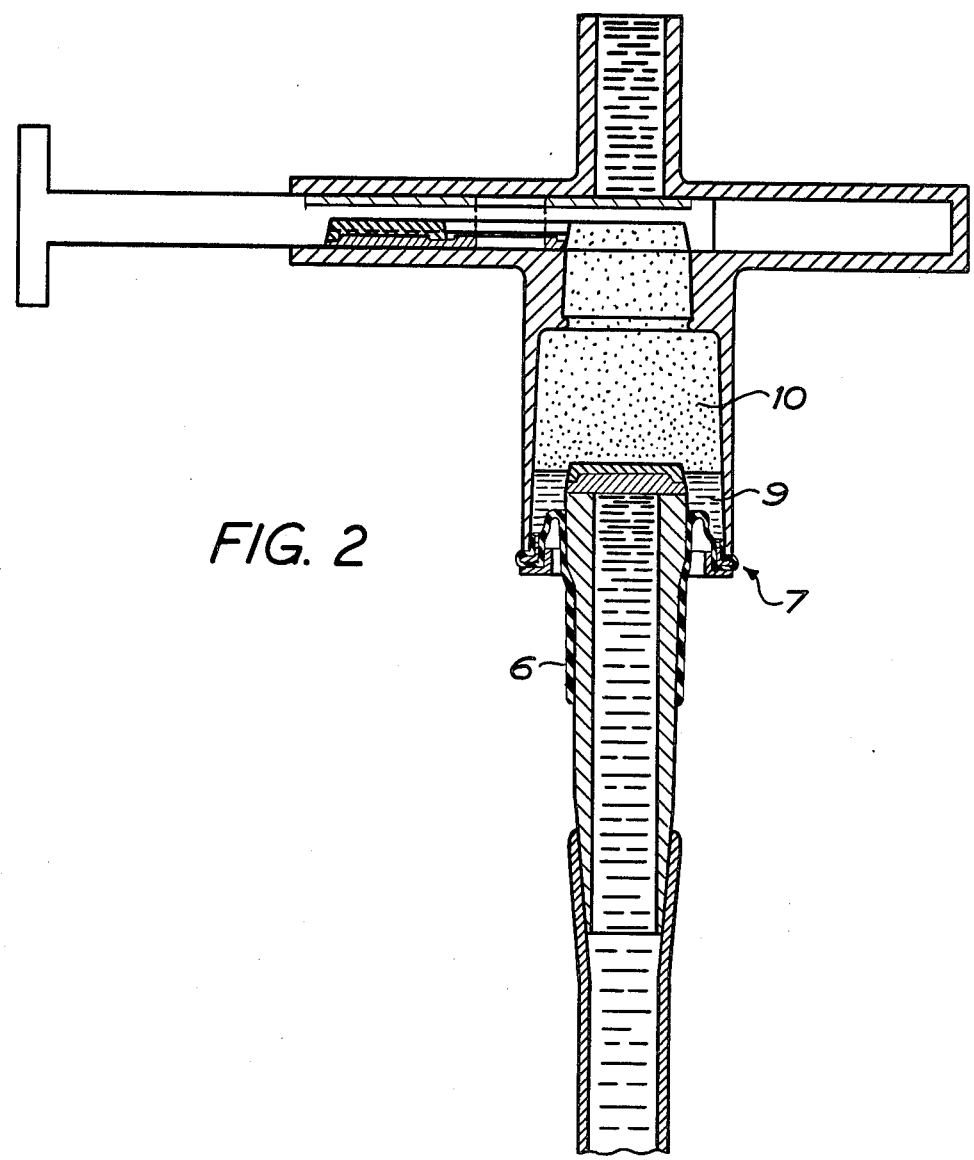
FIG. 2 shows the coupling components according to FIG. 1 during initial engagement.

FIG. 2 illustrates the coupling components during initial engagement, whereby the disinfectant is present in the cavity 10. By making the casing 6 elastic, this will expand somewhat during the continued insertion of the coupling element 1 into the coupling housing 2.

Figure 3:
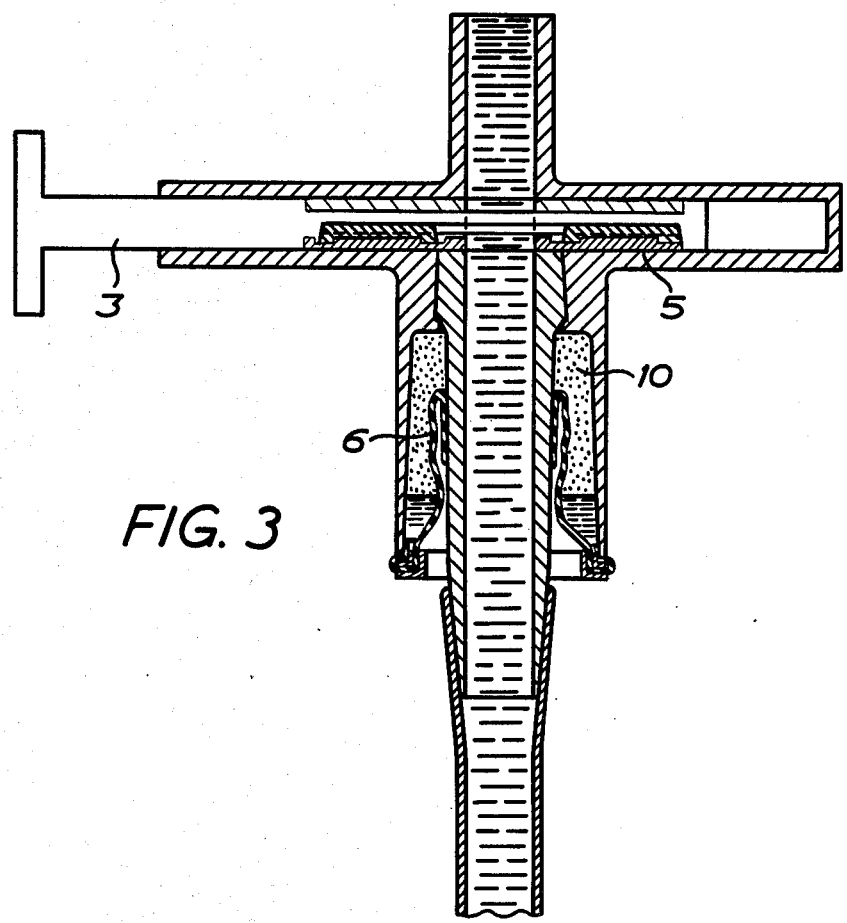
FIG. 3 shows the coupling in the engaged position which permits through-flow.

FIG. 3 illustrates the two coupling components 1 and 2 in an engaged and locked position, said locking being achieved by displacement of the slide 3, i.e. the coupling permits free passage through both coupling components. However, external locking can also be provided between the coupling element 1 and the coupling housing 2, i.e. the coupling components should be capable of being locked in an engaged position without a free passage necessarily existing between the coupling components. This facilitates operation of the coupling by preventing the casing 6 pushing the coupling components apart. Such a locking device between the coupling components can for example comprise a spring lock, etc.

Figure 4:
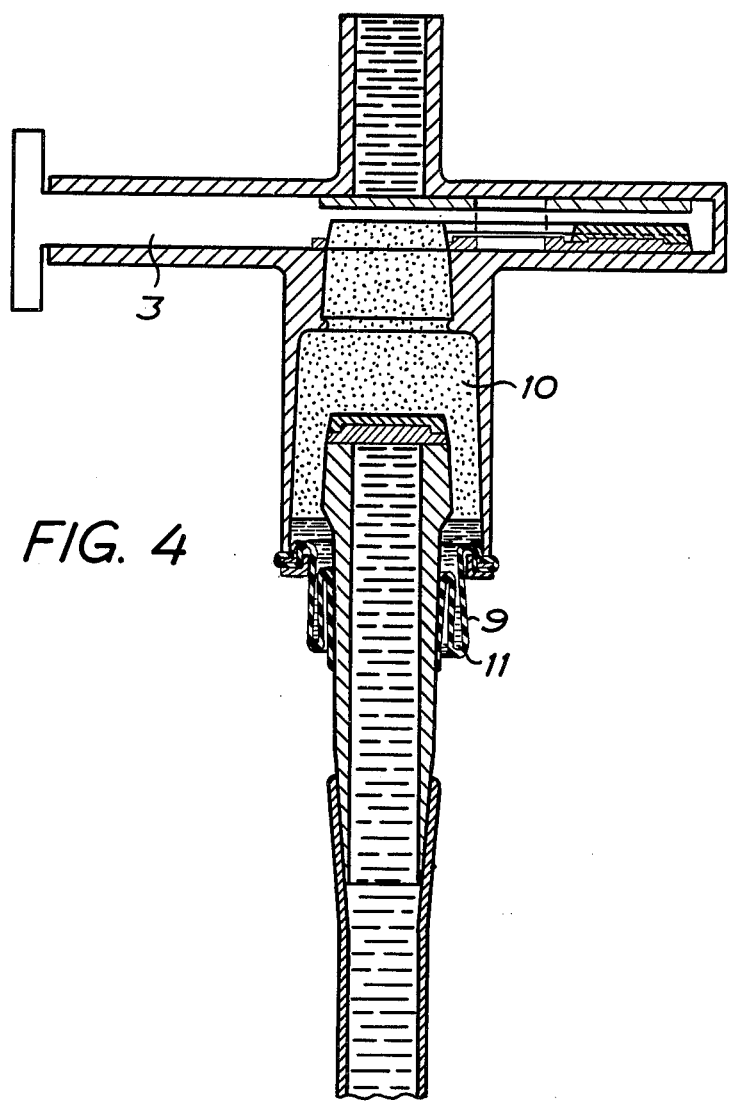
FIG. 4 illustrates the coupling in a position wherein the coupling element is being disengaged from the coupling housing.

When separating the coupling components (FIG. 4), the disinfectant 9 collects in the folded portion 11 of the casing, which means that a thin film of disinfectant will be present between the outside wall of the coupling element 1 and the casing 6 when the coupling element is removed completely from the coupling housing 2.

The coupling element 1 with the casing 6 arranged thereon can be supplied complete with liquid disinfectant, which means that a cover 12 (FIG. 1) of a suitable type has to be provided at the free end 6a of the casing 6.

Disinfectant is replenished as required in the casing 6.

I claim:

1. A coupling comprising a coupling element and a coupling housing to be connected with said coupling element said coupling housing including a socket for receiving one end of the coupling element therein, said coupling element having a valve for closing the coupling element at one end thereof, a thin flexible casing which surrounds at least a part of the coupling element and projects axially from said one end thereof, said casing defining together with said coupling element and said coupling housing a cavity for accommodating a disinfection agent therein, and means at the projecting end of said casing for substantially fluid-tight connection of the casing to one end of said coupling housing, said casing allowing said coupling element to be introduced into said socket while passing through the disinfecting fluid.

2. A coupling as claimed in claim 1 further comprising a locking device for locking together the coupling element and the coupling housing when the coupling element is fully introduced into said socket.

3. A coupling as claimed in claim 1 further comprising a cover for closing said coupling element.

* * * * *